(12) United States Patent
Viertl et al.

(10) Patent No.: US 6,288,537 B1
(45) Date of Patent: Sep. 11, 2001

(54) EDDY CURRENT PROBE WITH FOIL SENSOR MOUNTED ON FLEXIBLE PROBE TIP AND METHOD OF USE

(75) Inventors: John R. M. Viertl; Martin K. Lee, both of Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/468,845

(22) Filed: Dec. 22, 1999

(51) Int. Cl.[7] .................. G01N 27/82; G01N 27/90; G01B 7/06; G01R 33/12

(52) U.S. Cl. .................. 324/230; 324/240; 324/229; 324/260

(58) Field of Search .................. 324/222, 220, 324/238, 654, 671, 229, 207.17, 230, 240, 262

(56) References Cited

U.S. PATENT DOCUMENTS

| | | |
|---|---|---|
| 3,475,681 | 10/1969 | Nerwin, Jr. et al. . |
| 3,737,764 | 6/1973 | Dufayet . |
| 3,826,132 | 7/1974 | Fetner et al. . |
| 4,194,149 | 3/1980 | Holt et al. . |
| 4,268,791 | 5/1981 | Rogel et al. . |
| 4,480,225 | * 10/1984 | Vance et al. .................. 324/238 |
| 4,593,245 | 6/1986 | Viertl et al. . |
| 4,700,134 | * 10/1987 | Scharton et al. .................. 324/220 |
| 4,797,613 | * 1/1989 | Wentzell .................. 324/220 |
| 5,293,132 | * 3/1994 | Koch .................. 324/671 |
| 5,341,678 | 8/1994 | Kervinen . |
| 5,389,876 | 2/1995 | Hedengren et al. . |
| 5,801,532 | 9/1998 | Patton et al. . |
| 5,841,277 | 11/1998 | Hedengren et al. . |
| 5,903,147 | 5/1999 | Granger, Jr. et al. . |
| 5,915,277 | 6/1999 | Patton . |

* cited by examiner

Primary Examiner—Safet Metjahic
Assistant Examiner—T. R. Sundaram
(74) Attorney, Agent, or Firm—Nixon & Vanderhye P.C.

(57) ABSTRACT

A pair of copper coils are embedded in the foil strip. A first coil of the pair generates an electromagnetic field that induces eddy currents on the surface, and the second coil carries a current influenced by the eddy currents on the surface. The currents in the second coil are analyzed to obtain information on the surface eddy currents. An eddy current probe has a metal housing having a tip that is covered by a flexible conductive foil strip. The foil strip is mounted on a deformable nose at the probe tip so that the strip and coils will conform to the surface to which they are applied.

11 Claims, 5 Drawing Sheets

# EDDY CURRENT PROBE WITH FOIL SENSOR MOUNTED ON FLEXIBLE PROBE TIP AND METHOD OF USE

This invention was made with Government support under Contract No. DE-FC21-95MC-31176 awarded by the Department of Energy. The Government has certain rights in this invention.

FIELD OF THE INVENTION

This invention relates to an eddy current probe for detecting flaws and thicknesses in the surface and sub-surface region of a conductive material by inducing and measuring an eddy current on the surface of the material. The invention is particularly suitable for inspecting surface coatings, sub-surface cracks and surface flaws in metallic and semi-conductive materials. The eddy current probe may also be used to measure the thickness of an insulating coating on a metallic or semi-conductive material.

BACKGROUND OF THE INVENTION

Eddy current probes are used to inspect the surfaces of metal and semiconductive objects. In one application, eddy current probes are applied to inspect the surfaces of metallic objects, such as rotor blades of steam and gas turbines. Eddy current probes provide a non-destructive test for inspecting the rotor blades.

Eddy current probes are applied to the surface (or near to the surface) of the metallic or semiconductive object being inspected. To induce a useful eddy current on a conductive surface, the probe applies an electromagnetic field to the surface to induce eddy currents. This electromagnetic field is generated by current in an inducing (driving) coil of the eddy current probe. The eddy currents induced on a surface have relatively low energy and are best detected by probes placed on (or at least near) the surface. A sense coil in the eddy current probe is placed against a surface so that the sense coil current is influenced by the surface eddy currents. The effects on the sense coil currents by the surface eddy currents are measured by processing circuits associated with the probe. To measure the thickness of an insulating coating, the eddy currents on a conductive or semi-conductive surface below the coating is measured. This eddy current measurement is indicative of the coupling between the eddy current probe and the having the coating. This coupling between the probe and part is a function of the distance between the probe coils and the conductive or semi-conductive surface below the insulating coating. Accordingly, the thickness of the coating may be determined from the eddy currents measured by the probe.

Many of the objects to be inspected with an eddy current probe have complex surface contours. For example, a rotor blade has a twisted airfoil column, a flange and a pine tree root. Applying an eddy current probe to the surface contours of a rotor blade or other object is difficult, especially with robot controlled inspection instrument. The tip of the eddy current probe may not conform to the surface of the object being inspected. If good contact is not established between the eddy current probe and the surface, or if there is an air gap between the probe and surface, the probe may be unable to accurately measure the eddy currents induced on the conductive or semi-conductive the surface. Similarly, the tip of the probe may be broken if it is too forceably driven onto the surface. Accordingly, there is a need for an eddy current probe that is sufficiently flexible to conform to odd surface shapes, and that is capable of withstanding impacts with a surface being inspected.

BRIEF SUMMARY OF THE INVENTION

A novel eddy current probe has been developed having a pair of conductive coils embedded in a foil strip and backed by a deformable nose at the sensory tip of the probe. The foil strip is wrapped over the deformable nose to provide a flexible backing to the coils in the strip. This flexibility allows the coils, strip and nose to conform to a surface being inspected and withstand an impact with that surface. Of the pair of conductive coils, the inducing coil (the driving coil) induces an eddy current on the surface of an object being inspected. The other coil (sense coil) carries a current induced by the magnetic flux from the eddy currents on the conductive or semi-conductive surface. The induced current in the sense coil is indicative of the surface eddy currents, and is used to measure the strength of those surface eddy currents on the object being inspected.

The foil strip of the eddy current probe sandwiches the inducing and sense coils between two flexible films that are laminated together. The coils may be arranged at the center of the foil strip, and connected to terminals at the ends of the strip by parallel tracks of wire extending laterally along the length of the films. At a center section of the foil, each of the coils may be arranged in a rectangular and spiraling coil. The coils may be nested together in the strip.

The foil strip with the embedded coils is wrapped over a flexible nose of the eddy current probe. The nose provides a soft base to support the film and coils. The nose may be formed of a silicon rubber or other deformable material. For the grinding applications, a rubber material, such as VITON™, that is more impervious to the effects of cutting fluid may be needed. The base of the nose is mounted on the probe housing. The outer surface of the nose may be a rounded ridge or have some other shape conforming to the intended surface to be measured. As the nose is pressed against a surface, it deforms and conforms to that surface. The nose is resilient and returns to its original shape when lifted from a surface. The foil strip is wrapped over the nose to fit smoothly over the outer surface of the nose. Accordingly, the nose provides a supporting surface for the foil and coils, and allows the foil to flex when in contact with another surface.

As the eddy current probe is positioned on the surface of an object being inspected, the sensory tip of the probe is pressed against the surface with sufficient force to deform the nose, and cause the foil and coils to conform to the contours of the surface. As the coil conforms to the surface, the coils are properly positioned against the surface to induce and measure an eddy current on the surface. By flattening the coils against the surface, the coils are inherently positioned to be immediately adjacent the surface and to eliminate air pockets between the coils and the surface. Because the inducing coil is at the surface, the current in that coil need be relatively modest to induce measurable eddy currents on the conductive or semi-conductive surface. Similarly, the proximity of the sensing coil to the surface allows for relatively large currents to be induced in that coil due to the eddy currents on the surface. Accordingly, the ability to conform the coils to and against a surface of the object being measured is an advantageous feature of the present eddy current probe.

Applying the foil strip and coils of the present eddy current probe directly against the surface is due, in part, to the deformable nose on the eddy current probe. As the probe moves into contact with the surface, the film is pressed firmly against the surface by the nose of the probe. As the nose deforms under the force between the nose and the surface, the film is flattened against the surface and thereby provides good contact between the film strip and surface. Accordingly, the deformable nose is helpful in causing the coils to conform to a surface and, thus, to providing good eddy current measurements.

DETAILED DESCRIPTION OF THE INVENTION

Figure 1:
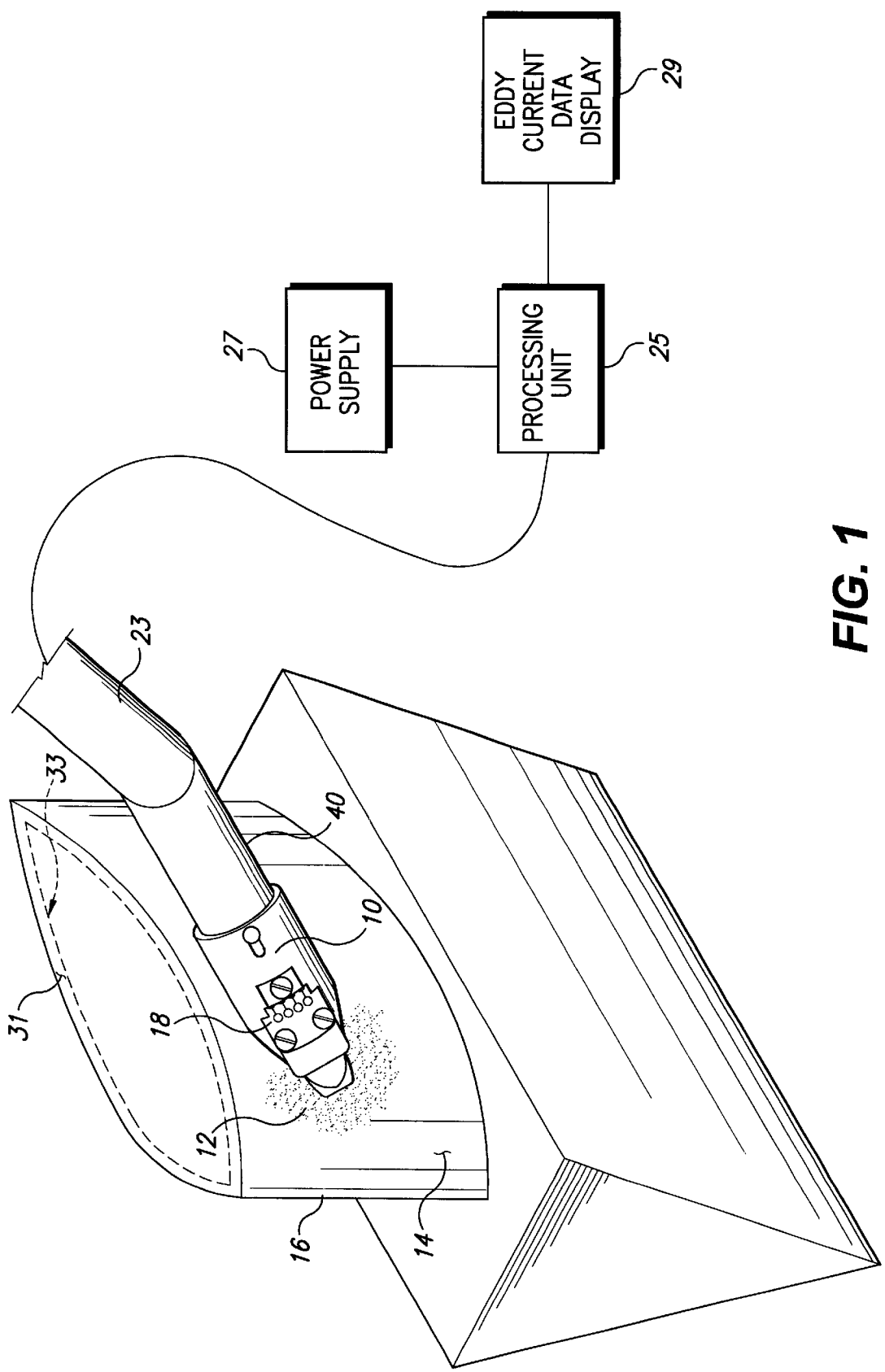
FIG. 1 shows an eddy current probe measuring eddy currents at the surface of an object.

FIG. 1 shows an eddy current probe 10 induces and senses eddy currents 12 on the surface 14 of an object 16, e.g., a turbine blade, that is being inspected with the probe. The tip 18 of the eddy current probe has a inducing coil 20 (or drive coil) carrying AC current from a power supply 27. The AC current from the power supply flows through the inducing coil 20 generates a magnetic field surrounding that coil. The magnetic flux from the inducing coil generates eddy currents 12 on the surface 14 and in the vicinity of the probe tip.

The tip 18 of the eddy current probe 10 has a sensing coil 22. The sensing coil is sensitive to the eddy currents 12 on the surface of the object being inspected and in the vicinity of the eddy current probe tip. The eddy currents affect the magnetic field in the immediate vicinity of the surface. The sensing coil 22 is in this magnetic field generated by the eddy currents on the surface. Magnetic flux from the eddy currents effect the current in sensing coil 22. The effects from the surface eddy currents on the current in the sensing coil are detected by processing circuits 25 coupled to the eddy current probe.

The eddy current probe may be moved from one surface location to another by a coordinate measuring machine 23 or computer numerical control (CNC) machine. As the eddy current probe moves from one surface location to another, eddy current measurements are made at each location and analyzed by the processing circuits 25. The eddy current data from the processing circuit is output to an eddy current display 29 or other device at which the eddy current data is correlated and evaluated with the surface locations at which that data was obtained.

The currents of the sense coil 20 in the eddy current probe 10 provide information on the eddy currents on the surface of the object being inspected. The current signals from the sensing coil of the eddy current probe are analyzed by the processing circuits to generate information regarding whether the eddy currents abruptly change at some surface location, which may indicate a flaw in the surface. The current signals from the sensing coil also provide information regarding the relative magnitude of the eddy currents at one surface location as compared to another surface location. The processing circuits generate information, in the form of reports, display images and/or graphs that show where on the surface of an object that the eddy currents are strong and where they are weak.

If a conductive surface has a non-conducting coating 31, then the eddy currents may flow on the conductive sub-surface 33 below the coating. The eddy current probe is separated from the eddy currents by the thickness of the coating 31. The relative strength of the eddy currents as sensed by the probe may be due to the coating thickness over the conductive surface. Accordingly, the relative eddy current strength of the signal pick-up by the sensing coil may be used to measure the thickness of the coatings 31 over the sub-surface 33. By comparing information obtained from the probe on where the eddy currents are strong and weak, the relative thickness of a coating on the surface of the object may be determined.

Figure 2:
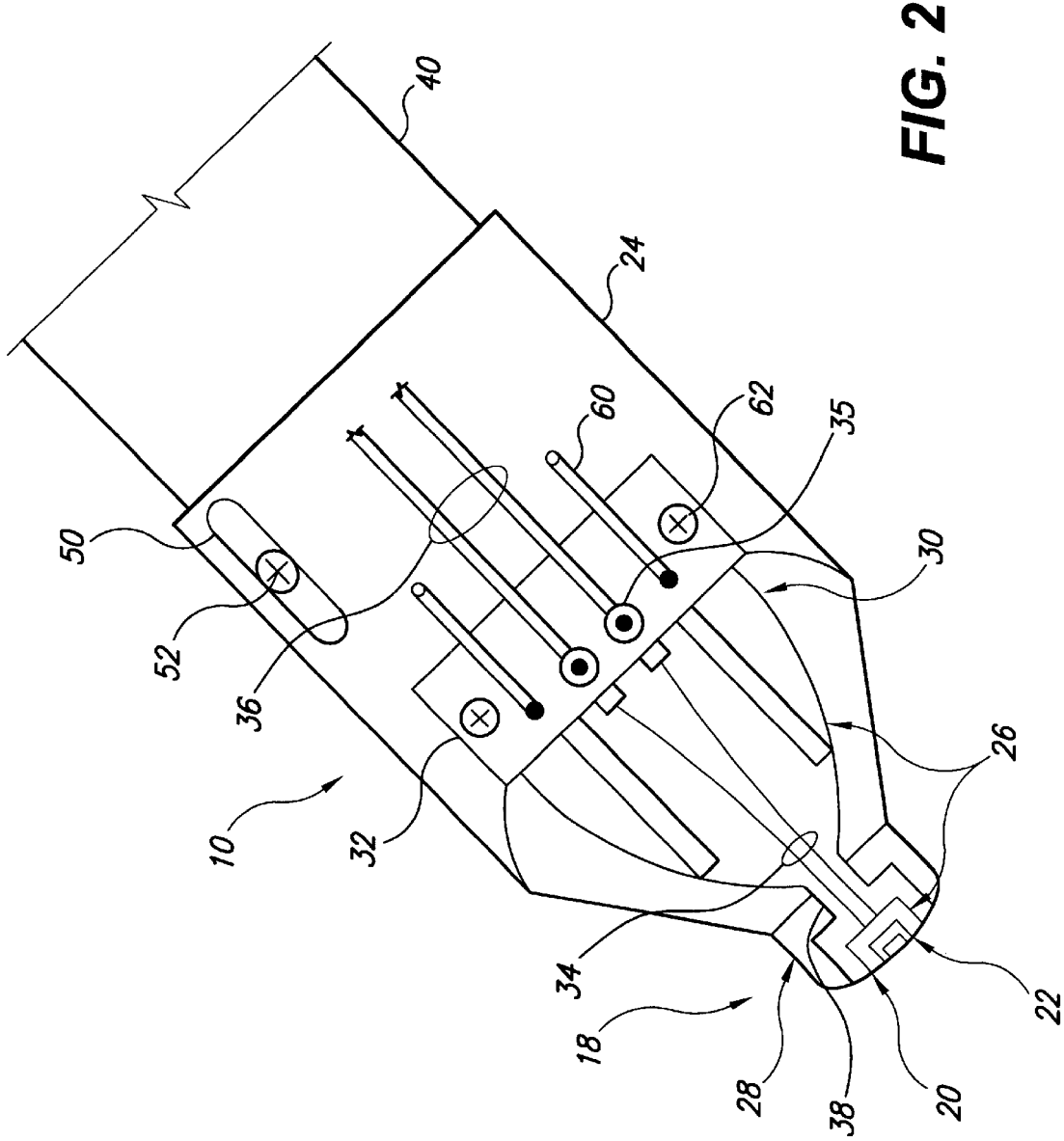
FIG. 2 is a close-up, side view of the eddy current probe shown in FIG. 1.

FIG. 2 shows one embodiment of an eddy current probe 10 having a bullet-shaped metal housing 24, a probe tip 18 at one end of the house, and a base 38 which provides a mounting for housing and probe. The tip of the probe includes the pair of inducing and sensing coils 20, 22 that are embedded in a foil strip 26. The strip 26 is wrapped over a nose 28 formed of a soft and formable material. The sensing coils 20, 22 in the strip 26 are aligned over the tip of the nose 28 in order to be at the outermost extremity of the eddy current probe. Opposite ends 30 (one end of shown in FIG. 1, and the other end is hidden from view) of the strip 26 are affixed to small sections of printed circuit board (PCB) 32 that is attached to the probe housing 24. Wires 34 in the foil strip connect the printed circuit board to the coils 20, 22. The PCB 32 has electrical terminals 35 that connect the wires and coils in the foil strip, to an external electrical connection. Lead wires 36 attached to the terminals of the PCB couple the coils and their wires to processing circuits 25 and the power supply 27. In addition, between the PCB and the tip of the nose, the foil strip necks down 38 to facilitate being wrapped around the nose of the probe.

The probe 10 may be attached to a coordinate measuring machine 23 or a CNC machine which precisely positions the tip of the probe at the surface of an object being inspected. The coordinate measuring machine locates the surface position at which an eddy current measurement is to be made. A computer (not shown) correlates the surface location of the probe with the eddy current data obtained from the probe. This correlation enables the eddy current data to be mapped to an image or drawing of the surface of the object being measured.

The eddy current probe 10 may be attached to a touch-trigger probe switch 40, such as a Renishawm™ TP2 switch. A touch-trigger probe switch generates a signal when the tip of the eddy current probe touches the surface of an object. When the eddy current probe 10 is attached to a touch-trigger probe 40, a signal is generated by the switch 40 when the tip 18 of the eddy current probe touches the surface of an object. The touch trigger probe switch may be adjusted to set the amount of force applied to the tip 18 of the probe 10 that will provoke the touch switch 40 into generating a signal. The force setting for the touch trigger switch 40 may chosen such that it is sufficient to cause the tip 18 of the eddy current probe to be pressed firmly against the surface of the object being measured and thereby deform the nose 28 and flatten the coils 20, 22 on the surface. The touch trigger switch ensures that the coils 20, 22 are firmly against a surface before generating a signal that the eddy current probe is in place at a surface. In addition, the touch trigger switch 40 ensures that the force between the probe tip 18 and a surface is of substantially the same magnitude of force each time an eddy current measurement is made at a surface. The signal from the touch trigger probe may also be used to start an eddy current measurement at the surface location selected by the coordinate measuring machine.

In operation, the coordinate-measuring machine 23 moves the eddy current probe to a predetermined position on the surface of the object being inspected. At that surface position, the tip of the tip eddy current probe is pressed against the surface until soft nose 28 of the probe deforms and causes the coils 20, 22 to conform to the contours of a surface. When the force applied to the tip of the probe by the surface exceeds the force setting of the touch trigger switch 40, a signal is generated by the switch that stops the movement of the eddy current probe by the coordinate measuring machine, and starts an eddy current measurement procedure. This process is repeated each time that the eddy current probe is moved to a new surface location on the object being inspected.

Figure 3:
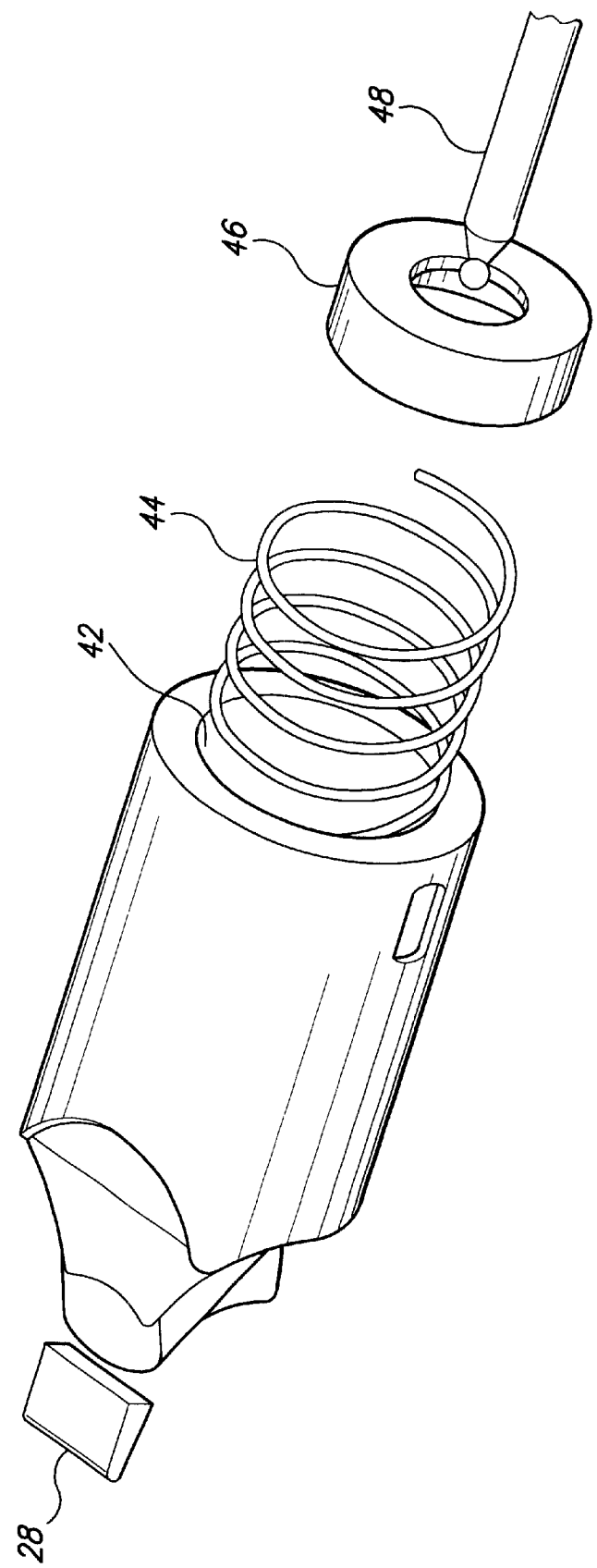
FIG. 3 is an exploded view of the components of the eddy current probe shown in FIG. 1.

FIG. 3 shows an exploded end view of eddy current probe 10. The housing 24 includes a circular recess 42 that receives a spring 44 and piston 46 used to couple the eddy current probe to a touch trigger switch. The cylindrical housing 24 fits onto a post at the end of a touch-trigger switch 40 (shown in FIG. 3 by the touch finger 48 of the switch). A slot 50 in the side of the housing receives a screw 52 extending out from the side of the touch-trigger switch. The slot and screw connection allows for limited reciprocal movement between the eddy current probe and the touch trigger switch. The piston 46 seats on the end of the touch trigger switch and the spring 44 biases the eddy current probe outward from the touch trigger switch. The stiffness of the spring should be firmer than the deformable nose 28 on the eddy current probe. As the tip 18 of the eddy current probe touches a surface, the nose deforms, and then the spring 44 allows the eddy current probe to slide slightly into the touch trigger switch until the trigger finger 48 touches the bottom of the recess 42 in the housing 24 of the eddy current probe. As the finger 48 touches the bottom of the probe recess, the touch trigger switch 40 generates a signal to stop the further movement of the eddy current probe by the coordinate measuring machine.

The soft nose 20 is attached to the front end of the housing 24 by adhesive. The nose may be formed of silicone rubber or Viton™ and have an outer surface shaped as a rounded ridge. The shape of the nose may depend on the contours of the surface against which the nose will be placed. The nose is intentionally deformable so as to form a flat contact area with a surface, when pressed against that surface. The coils 20, 22 and foil strip 26 are sandwiched between the contact area of the nose 20 and the surface to ensure that the coils are properly placed against the surface. Because the nose deforms, it and the coils can readily conform to irregular surface shapes or slight misalignments between the probe and the surface.

The foil strip 26 is wrapped over the outer surface of the nose 20. The nose provides a backing and support for the foil strip. The foil strip may be attached to the nose by an adhesive and by securing the ends of the strip to the printed circuit board 32. The coils 20, 22 in the strip are aligned with the ridge of the nose 20 to be at the outer extremity of the eddy current probe.

Figure 4:
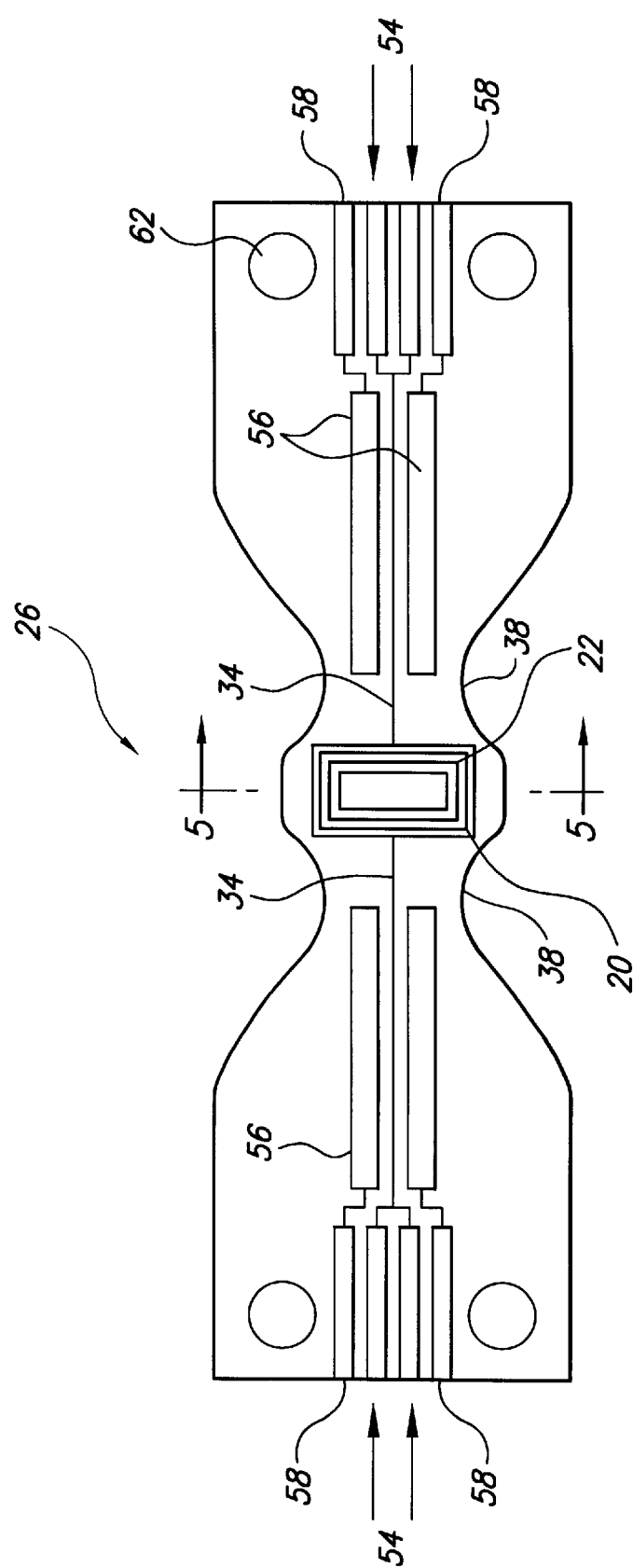
FIG. 4 is plan view of a flexible foil with embedded coils that is a component of the eddy current probe shown in FIG. 1.

FIG. 4 is plan view of the strip of flexible foil strip 26 with embedded coils 20, 22. The strip 26 is formed of an upper foil film and a lower foil film with the coils 20, 22 and wires 34 sandwiched between and on the foil strips. The foil strips are copper plated KAPTON™. An adhesive is used to laminate the upper and lower foil films and to seal the coils in the foil strip. The adhesive may be set with heat after the upper and lower foil films and coils have been assembled into the foil strip. The wire and coils are arranged between the films, and the film, wires and coils are laminated by heat to form the composite foil strip.

The coils 20, 22 may be arranged as a nest of rectangular wire loops that become smaller and smaller towards the center of the rectangular arrangement. Alternatively, the coils may be a wire that spirals in a circular arrangement. Such arrangements of coils are shown in commonly assigned U.S. Pat. No. 4,593,245, entitled "Eddy Current Method For Detecting A Flaw in Semi-Conductive Material".

Figure 5:
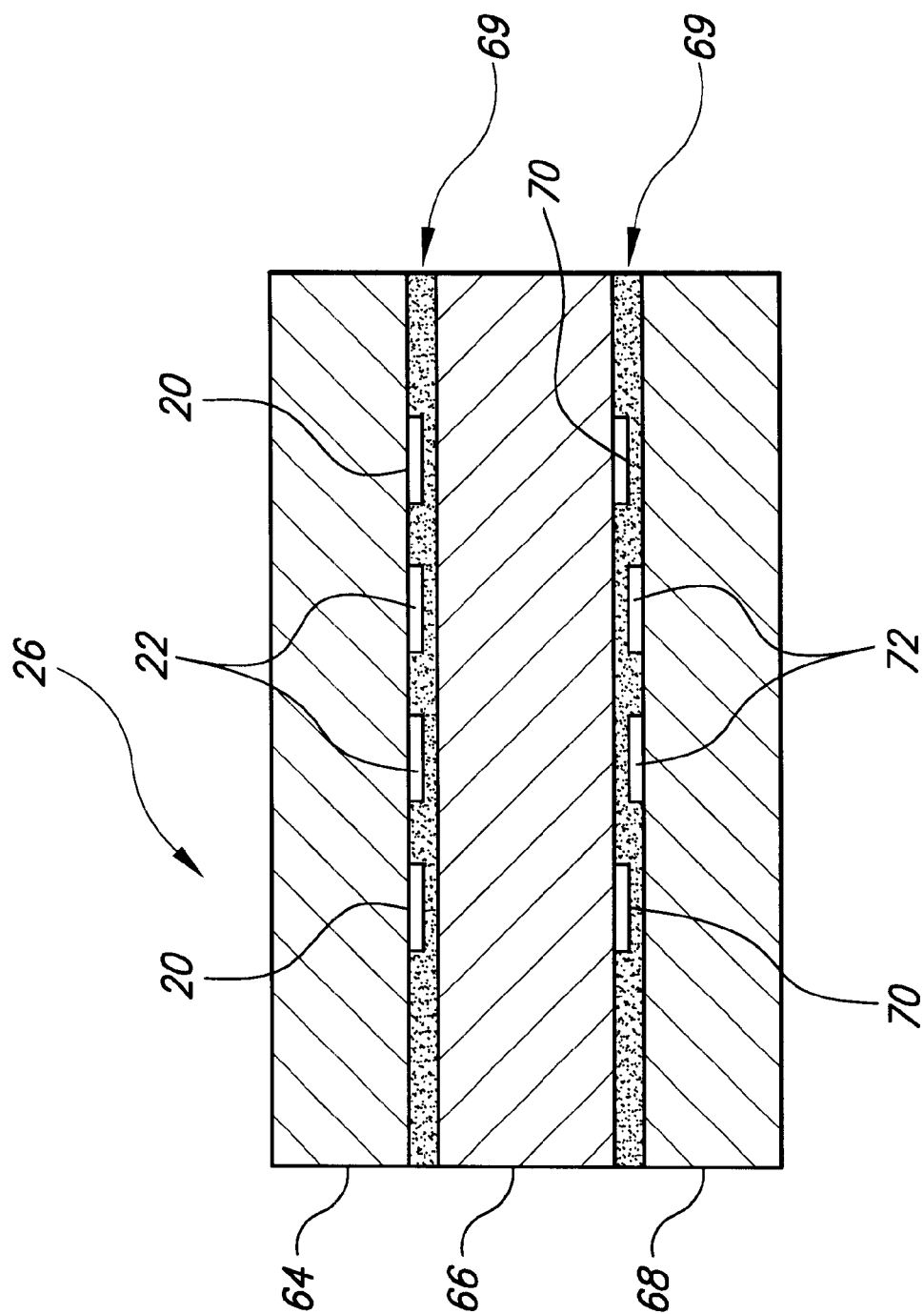
FIG. 5 is a cross-section view of the foil shown in FIG. 4 and taken along line 5—5.

FIG. 5 is a cross-sectional view of the foil which shows the laminated foil layers that support the coil structures. For example, the coil structure may distributed over the foil layers, L1 (64), L2 (66) and L3 (68), superimposed one over the other. Thermally sensitive adhesives 69 laminate the layers together. The top layer (L1) has one sense coil 22 and one inducing (drive) coil 20. The second layer (L2) has a second drive coil 70 and the third layer (L3) has a second sense coil 72. An electrical connection from one end of the drive coil in layer (L1) extends through that layer (L1) to the drive coil in the second layer (L2) to form a complete drive coil circuit. The return lead of the drive coil in the second layer (L2) is brought back through to layer (L1). The return lead for the drive coil circuit terminates on a gold plated contact on the top side of the first layer (L1) and adjacent the input lead to the drive coil in the first layer (L1). The sensing coil is also patterned on the first layer and extends though the second layer (L2) to connect with the sense coil on the third layer (L3). The return lead for the sense coil extends from the third layer (L3) through the second and first layers and terminates on a gold plated contact on the top side of the first layer. Indeed, all the electrical pads for connection to the coils may be brought to the top of layer L1.

The drive coils are wired in series. These are rectangular spiral coils. The sense coils are arranged as a single or a few turns on each layer (L1) and (L3). The sense coils may be also wired in series for applications to determine the thickness of a coating on a conductive surface. Other wiring combinations are possible, such as parallel, or dual, balanced pair for differential operation.

Each of these drive and sense coils in the first layer (L1) is carefully aligned with the drive or sense coil below it. The mounting holes are also carefully located with respect to the coil structure. Controlling these geometrical parameters provides the means of maintaining very consistent performance from probe foil to probe foil. The coils are fabricated on thin KAPTON™ sheets that support the copper metallization patterns. Using reference marks on the layers, the sheets are jointed together with an adhesive. Typically, an un-plated KAPTON™ sheet is bonded to both the top of L1 and the bottom of L3. The gold plated contact pads are not covered with a KAPTON™ layer. The wire-coils may also have other than rectangular arrangements, such as circular, spiral, or elliptical coil arrangements.

The foil strip includes the inducing coil 20 and the sensing coil 22, and the wires 34 that extend from the coils to the metal contacts 54 at the opposite ends of the strip. The wires 34 leading to the inducing coil 20 may extend to a pair of contacts 54 at the right end of the strip, and the wires that lead to the sensing coil 22 may extend to another pair of contacts 54 at the left end of the strip, or vice versa. The wires and coils may be fine copper wires having a width of about 2 thousandths of an inch (2 mils) and a thickness between 0.1 to 0.5 mils. Ground strips 70 are arranged on opposite sides of the wires extending from the coils to the contacts 54. The ground strip is a conductive strip, e.g., copper, that provides electromagnetic shielding for the coils and wires. The ground strips may have contacts 58 that are connected to conductive terminals 60 (FIG. 2) tuned to the ground strip. The ends of the foil strip 26 have holes 60 through which screws 62 (FIG. 2) extend to fasten the strip and printed circuit board 32 to the probe housing 24.

The preferred embodiment of the invention has been described herein. The invention is not limited to the preferred embodiment, but rather covers the various modifications and equivalent arrangements included within the spirit and scope of the appended claims.

What is claimed is:

1. An eddy current probe comprising:

a housing;

a nose of deformable material attached to a tip of the housing;

a flexible strip wrapped over an outer surface of the nose, wherein the flexible strip includes an inducing coil and a sensing coil, a coupling for the inducing coil for connecting the inducing coil to a power supply, and for the sensing coil for connecting the sensing coil to an eddy current signal processing system.

2. An eddy current probe as in claim 1 wherein the housing is connectable to a touch trigger switch.

3. An eddy current probe as in claim 1 wherein the flexible strip includes a pair of conductive lines between the inducing coil and a connector pair at the first end of the flexible strip.

4. An eddy current probe as in claim 3 wherein the flexible strip includes a second pair of conductive lines between the sensing coil and a second end of the flexible strip that is opposite to the first end.

5. An eddy current probe as in claim 4 wherein the flexible strip includes ground shields bordering the conductive lines extending from the sensing coil.

6. An eddy current probe as in claim 1 wherein the outer surface of the nose space has a rounded ridge shape.

7. An eddy current probe as in claim 2 wherein the nose space comprises silicon rubber.

8. An eddy current probe as in claim 1 wherein the housing has a cylindrical body with a recess in one end to receive a finger of the touch trigger switch.

9. An eddy current probe as in claim 8 wherein the recess further receives a coil spring and a piston which engages a touch trigger switch.

10. A method for measuring an eddy current on a surface using an eddy current probe comprising the following steps:

a) positioning a probe tip onto the surface of the object being inspected;

b) deforming the tip of the probe by pushing the probe tip against the surface;

c) as the tip of the probe is deformed, conforming inducing and sensing coils at the tip of the eddy current probe to the surface, and purging air gaps from between the coils and the surface;

d) applying a current to the inducing coil to generate an eddy current on the surface; and e) detecting the surface eddy current by sensing currents generated by the eddy currents in the sensing coil of the probe.

11. A method for measuring an eddy current as in claim 10 further comprising the step of:

f) determining the thickness of a non-conductive coating the object being measured by measuring the eddy currents induced by the inducing coil on a conductive surface underlying the coating.

* * * * *